United States Patent
Delfort et al.

(10) Patent No.: US 10,618,866 B2
(45) Date of Patent: Apr. 14, 2020

(54) METHOD FOR SYNTHESISING PARTIALLY N-HYDROXYETHYLATED TERTIARY 1,6-HEXANEDIAMINES

(71) Applicant: IFP Energies Nouvelles, Rueil-Malmaison (FR)

(72) Inventors: Bruno Delfort, Paris (FR); Julien Grandjean, Lyons (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 0 days.

(21) Appl. No.: 16/062,152

(22) PCT Filed: Dec. 12, 2016

(86) PCT No.: PCT/EP2016/080669
§ 371 (c)(1),
(2) Date: Jun. 14, 2018

(87) PCT Pub. No.: WO2017/102659
PCT Pub. Date: Jun. 22, 2017

(65) Prior Publication Data
US 2019/0002392 A1    Jan. 3, 2019

(30) Foreign Application Priority Data
Dec. 17, 2015   (FR) ..................... 15 62671

(51) Int. Cl.
*C07C 213/04* (2006.01)
*C07C 209/16* (2006.01)
(Continued)

(52) U.S. Cl.
CPC .......... *C07C 213/04* (2013.01); *C07C 209/16* (2013.01); *C07C 209/50* (2013.01);
(Continued)

(58) Field of Classification Search
None
See application file for complete search history.

(56) References Cited

U.S. PATENT DOCUMENTS

2005/0164903 A1   7/2005  Ko

OTHER PUBLICATIONS

International Search Report PCT/EP2016/080669 dated Apr. 5, 2017.
(Continued)

*Primary Examiner* — Sudhakar Katakam
*Assistant Examiner* — Jennifer C Sawyer
(74) *Attorney, Agent, or Firm* — Millen White Zelano and Branigan, PC; Csaba Henter

(57) ABSTRACT

The invention relates to a synthesis method for at least one nitrogen compound belonging to the family of partly N-hydroxyethylated tertiary 1,6-hexanediamines with general formula (I) as follows:

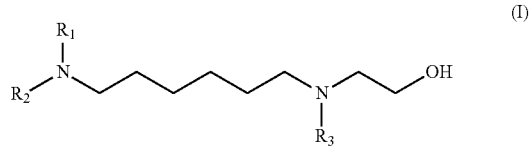

wherein radicals $R_1$, $R_2$, $R_3$ are each selected indiscriminately among a methyl radical and a hydroxyethyl radical, and at least one radical among $R_1$, $R_2$, $R_3$ is a methyl radical, comprising at least a first reaction between a first halogen atom-free precursor compound and a second halogen atom-free precursor compound.
The first precursor compound comprises a carbon skeleton consisting of a linear sequence of 6 carbon atoms with the
(Continued)

4 central carbon atoms bonded each to 2 hydrogen atoms and the carbon atoms in alpha and omega position not bonded to a halogen atom.

15 Claims, 4 Drawing Sheets

(51) Int. Cl.
    *C07C 209/50*     (2006.01)
    *C07C 213/08*     (2006.01)
    *C07C 231/02*     (2006.01)
    *C07C 249/02*     (2006.01)
    *C07C 211/12*     (2006.01)
    *C07C 215/14*     (2006.01)
    *C07C 233/05*     (2006.01)
    *C07C 235/08*     (2006.01)

(52) U.S. Cl.
    CPC .......... *C07C 211/12* (2013.01); *C07C 213/08* (2013.01); *C07C 215/14* (2013.01); *C07C 231/02* (2013.01); *C07C 233/05* (2013.01); *C07C 235/08* (2013.01); *C07C 249/02* (2013.01)

(56) References Cited

OTHER PUBLICATIONS

M. Ishidate: "Studies on Carcinostatic Substances. XVIII. Anticancer Action of N, N'-Bis (2-chloroethyl)-N, N'-dimethylpolymethylenediamines", Chemical and Pharmaceutical Bulletin, Jan. 1, 1958 (Jan. 1, 1958), pp. 164-169, XP055291401.
Clarke H T et al: "The Action of Formaldehyde on Amines and Amino Acids", Journal of the American Chemical Society, American Chemical Society, US, vol. 55, No. 11, Jan. 1, 1933 (Jan. 1, 1933), pp. 4571-4587, XP002402949, ISSN: 0002-7863.
Nie J et al: "Synthesis and photopolymerization of N,N'-dimethyl,-N,N'-di(methacryloxy ethyl)-1,6-hexanediamine as a polymerizable amine coinitiator for dental restorations", Biomaterials, Elsevier Science Publishers BV., Barking, GB, vol. 23, No. 4, Feb. 15, 2002 (Feb. 15, 2002), pp. 1221-1226, XP004348141, ISSN: 0142-9612.

US 10,618,866 B2

METHOD FOR SYNTHESISING PARTIALLY N-HYDROXYETHYLATED TERTIARY 1,6-HEXANEDIAMINES

FIELD OF THE INVENTION

The present invention relates to the synthesis of partly N-hydroxyethylated tertiary 1,6-hexanediamines.

BACKGROUND OF THE INVENTION

Partly N-hydroxyethylated tertiary 1,6-hexanediamines can be of interest for various applications.

Partly N-hydroxyethylated tertiary 1,6-hexanediamines can be advantageously used for example for deacidizing acid gases, whether natural gas or combustion fume gas. Acid gas deacidizing is understood to be the reduction of the proportion, in these gases, of acid compounds such as hydrogen sulfide ($H_2S$), carbon dioxide ($CO_2$), carbon oxysulfide (COS), carbon disulfide ($CS_2$).

Partly N-hydroxyethylated tertiary 1,6-hexanediamines can go into formulations leading to polymers, notably polyurethanes.

Partly N-hydroxyethylated tertiary 1,6-hexanediamines can be precursor compounds for molecules finding applications in other fields of chemistry.

Among the partly N-hydroxyethylated tertiary 1,6-hexanediamines, the synthesis of N,N'-dimethyl-N,N'-di(2-hydroxyethyl)-1,6-hexanediamine with formula ($I_2$) below, which involves using halogenated precursor reactants, is well known.

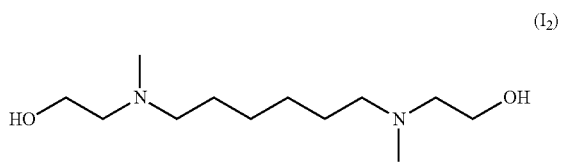

($I_2$)

Document US-2005/0,164,903 describes for example the synthesis of N,N'-dimethyl-N,N'-di(2-hydroxyethyl)-1,6-hexanediamine through a condensation reaction between one mole of 1,6-dichlorohexane and two moles of 2-(methylamino)ethanol. This condensation reaction inevitably leads to two moles of hydrochloric acid. Purification of the amine requires converting the hydrochloric acid to salt by reaction with a base, for example converting it to sodium chloride after reaction with soda or with sodium carbonate.

Ishidate et al., 1958 («Studies on carcinostatic substances. XVIII. Anticancer action of N,N'-bis(2-chloroethyl)-N,N'-dimethylpolymethylenediamines», Chemical & Pharmaceutical Bulletin (1958), vol. 6, pp. 164-169) describe the synthesis of N,N'-dimethyl-N,N'-di(2-hydroxyethyl)-1,6-hexanediamine through a condensation reaction between one mole of 1,6-dibromohexane and two moles of 2-(methylamino)ethanol. This condensation reaction inevitably yields two moles of hydrobromic acid. Purification of the amine requires then converting the hydrobromic acid to salt by reaction with a base, for example converting it to sodium bromide after reaction with soda or with sodium carbonate.

The article by Nie and Bowman, 2002 («Synthesis and photopolymerization of N,N'-dimethyl,-N,N'-di(methacryloxyethyl)-1,6-hexanediamine as a polymerizable amine coinitiator for dental restorations» Biomaterials 23, 2002, pp 1221-1226) describes the synthesis of N,N'-dimethyl-N,N'-di(2-hydroxyethyl)-1,6-hexanediamine through a condensation reaction between N,N'-dimethyl-1,6-hexanediamine and 2-bromoethanol in the presence of soda. This synthesis pathway generates two moles of sodium bromide per mole of N,N'-dimethyl-N,N'-di(2-hydroxyethyl)-1,6-hexanediamine.

Ishidate et al., 1958 («Studies on carcinostatic substances. XVIII. Anticancer action of N,N'-bis(2-chloroethyl)-N,N'-dimethylpolymethylenediamines», Chemical & Pharmaceutical Bulletin (1958), vol. 6, pp. 164-169) also describe the synthesis of N,N'-dimethyl-N,N'-di(2-hydroxyethyl)-1,6-hexanediamine in 4 steps from 1,6-hexanediamine, the first step being the reaction between one mole of 1,6-hexanediamine and two moles of tosyl chloride or p-toluenesulfonyl chloride leading to one mole of N,N'-dimethyl-N,N'-ditosyl-1,6-hexanediamine and two moles of hydrochloric acid. Purification of the reaction product requires converting the hydrochloric acid to salt by reaction with a base, for example converting it to sodium chloride after reaction with soda or with sodium carbonate.

Ishidate et al., 1958 («Studies on carcinostatic substances. XVIII. Anticancer action of N,N'-bis(2-chloroethyl)-N,N'-dimethylpolymethylenediamines», Chemical & Pharmaceutical Bulletin (1958), vol. 6, pp. 164-169) also describe the synthesis of N,N'-dimethyl-N,N'-di(2-hydroxyethyl)-1,6-hexanediamine in 3 steps from 1,6-dibromohexane, the first step being the reaction between one mole of 1,6-dibromohexane and two moles of methylamine tosylate or N-methyl-p-toluenesulfonamide leading to one mole of N,N'-di(p-tosyl)hexanediamine and two moles of hydrobromic acid. Purification of the amine requires converting the hydrobromic acid to salt by reaction with a base, for example converting it to sodium bromide, after reaction with soda or with sodium carbonate.

In the synthesis modes of the aforementioned prior art, the reactions produce salts in parallel to the wanted products. The salts formed need to be separated from the medium, for example by filtration, centrifugation or washing. These synthesis pathways which require management and removal of a significant amount of salts do not meet the current conditions relative to a green and sustainable chemistry. Extension of these synthesis pathways to an industrial scale is therefore not desirable.

GOALS AND SUMMARY OF THE INVENTION

The inventors have found that some partly N-hydroxyethylated tertiary 1,6-hexanediamines with general formula (I) as defined below can be prepared according to a procedure using no halogenated compound, such as for example 1,6-dichlorohexane or 1,6-bromohexane or another 1,6-dihalohexane, and no other halogenated compound such as, for example, 2-bromoethanol or another 2-haloethanol, and no reactant belonging to the family of tosyl halogenides, such as tosyl chloride for example. The inventors have found that these partly N-hydroxyethylated tertiary 1,6-hexanediamines can be prepared according to a procedure generating no salt, which is favourable for considering an industrial development.

The synthesis method according to the invention systematically uses precursor starting materials free from halogen atoms and it is based on reactions involving no halogenated organic reactant.

In particular, the synthesis method according to the invention uses a family of halogen atom-free precursors having a carbon skeleton that consists of a linear sequence of 6 carbon atoms where the carbon atoms in position 1 and 6, i.e. in alpha and omega position, are not bonded to a halogen atom such as, for example, a chlorine or bromine atom.

This family of precursors has a linear sequence of 6 carbon atoms where the 4 central carbon atoms are bonded each to 2 hydrogen atoms and the 2 carbon atoms in position 1 and 6, i.e. in alpha and omega position, are each bonded, either:

- by a single bond to a nitrogen atom and, in this case, the precursor is 1,6-hexanediamine,
- by a single bond to an oxygen atom and, in this case, the precursor is 1,6-hexanediol,
- by a double bond to an oxygen atom and, in this case, the precursor is adipaldehyde,
- by a double bond to an oxygen atom and also by a single bond to an oxygen atom and, in this case, the precursor is adipic acid or an adipic acid diester.

In addition to this family of precursors, the other products used for leading to the partly N-hydroxyethylated tertiary 1,6-hexanediamines with general formula (I) are by no means halogenated organic compounds.

The compounds according to general formula (I) can be obtained from this family of precursors in, as the case may be, 1 to 3 reaction steps that will produce no hydrohalogenated acid.

The reactions involved in the synthesis method generate no salt to be separated and eliminated. These reactions generate in the synthesis method only co-products such as water and/or light alcohols.

In that sense, the invention is advantageously distinguished from the prior art.

The present invention thus provides a synthesis method for at least one nitrogen compound belonging to the family of partly N-hydroxyethylated tertiary 1,6-hexanediamines with general formula (I) as follows:

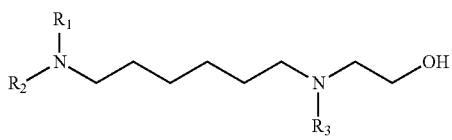

(I)

wherein radicals $R_1$, $R_2$, $R_3$ are each selected indiscriminately among a methyl radical and a hydroxyethyl radical, and at least one radical among $R_1$, $R_2$, $R_3$ is a methyl radical.

The method comprises n reaction steps, n ranging from 1 to 3, and none of the n reaction steps comprises a halogenated reactant.

The method comprises at least a first reaction between a first halogen atom-free precursor compound and a second halogen atom-free precursor compound, the first precursor compound comprising a carbon skeleton consisting of a linear sequence of 6 carbon atoms with the 4 central carbon atoms bonded each to 2 hydrogen atoms and the carbon atoms in alpha and omega position are not bonded to a halogen atom.

According to an embodiment of the invention, at least N,N'-dimethyl-N,N'-di(2-hydroxyethyl)-1,6-hexanediamine with formula ($I_2$) as follows is formed:

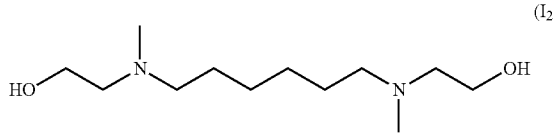

($I_2$)

According to an embodiment, the first precursor compound is 1,6-hexanediamine and the second precursor compound is ethylene oxide. The method then comprises:

- a first reaction step between the 1,6-hexanediamine and the ethylene oxide so as to form at least one intermediate compound selected from the list including N-(2-hydroxyethyl)-1,6-hexanediamine, N,N'-di(2-hydroxyethyl)-1,6-hexanediamine, N,N-di(2-hydroxyethyl)-1,6-hexanediamine and N,N,N'-tri(2-hydroxyethyl)-1,6-hexane-diamine;
- a second step of methylation of the primary or secondary amine functions of said at least one intermediate compound so as to form at least one compound according to general formula (I).

Preferably, the second methylation step is carried out by reaction between said intermediate compound, formaldehyde and hydrogen in the presence of a hydrogenation catalyst, or by reaction between said intermediate compound, formaldehyde and formic acid according to the Eschweiler-Clarke reaction.

Advantageously, the residual 1,6-hexanediamine that has not reacted at the end of the first reaction step is recycled to said first reaction step, after separation by distillation of said 1,6-hexanediamine from said at least one intermediate compound.

Advantageously, the molar ratio of ethylene oxide to 1,6-hexanediamine is less than or equal to 3/1, and preferably less than or equal to 2.5/1.

The method can further comprise, at the end of the first reaction step, at least one separation step, preferably by distillation, of at least one intermediate compound so as to form a specific compound meeting general formula (I) or a combination of specific compounds meeting general formula (I) at the end of the second methylation step.

According to an embodiment, the first precursor compound is 1,6-hexanediol and the second precursor compound is methylamine. The method then comprises:

- a first step of a condensation reaction between the 1,6-hexanediol and the methylamine, preferably in the presence of hydrogen and of a hydrogenation catalyst so as to form N,N'-dimethyl-1,6-hexanediamine;
- a second reaction step between the N,N'-dimethyl-1,6-hexanediamine and the ethylene oxide so as to form N,N'-dimethyl-N,N'-di(2-hydroxyethyl)-1,6-hexane-diamine.

According to an embodiment, the first precursor compound is adipaldehyde and the second precursor compound is methylamine.

In this case, the method can comprise:

- a first reaction step of condensation between the adipaldehyde and the methylamine, leading to 1,6-bis(methylimino)-hexane;
- a second reaction step of reduction of the 1,6-bis(methylimino)-hexane so as to form N,N'-dimethyl-1,6-hexanediamine;
- a third reaction step of ethoxylation of the N,N'-dimethyl-1,6-hexanediamine with ethylene oxide so as to form N,N'-dimethyl-N,N'-di(2-hydroxyethyl)-1,6-hexane-diamine.

Alternatively, the method can comprise a step of condensation of the adipaldehyde with the N-methyl-2-aminoethanol in the presence of hydrogen and of a hydrogenation catalyst so as to lead to N,N'-dimethyl-N,N'-di(2-hydroxyethyl)-1,6-hexanediamine.

According to an embodiment, the first precursor compound is adipic acid or an adipic acid diester.

In this case, the second precursor compound can be N-methyl-2-aminoethanol and the method then comprises the following two steps:
- a first reaction step of condensation of the N-methyl-2-aminoethanol with adipic acid or an adipic acid diester, said adipic acid diester being preferably dimethyl adipate or diethyl adipate, so as to form N,N'-dimethyl-N,N'-di(2-hydroxyethyl)-adipamide;
- a second step of reduction of the amide functions of the N,N'-dimethyl-N,N'-di(2-hydroxyethyl)-adipamide to tertiary amine functions so as to lead to N,N'-dimethyl-N,N'-di(2-hydroxyethyl)-1,6-hexanediamine.

Alternatively, the second precursor compound can be methylamine and the method then comprises the following three steps:
- a first step of condensation of the methylamine with adipic acid or an adipic acid diester, said adipic acid diester being preferably dimethyl adipate or diethyl adipate, so as to form N,N'-dimethyl-N,N'-adipamide;
- a second step of reduction of the amide functions of the N,N'-dimethyl-N,N'-adipamide to tertiary amine functions so as to lead to N,N'-dimethyl-1,6-hexanediamine, preferably by catalytic hydrogenation or through the action of hydrides, preferably lithium and aluminium hydride;
- a third step of ethoxylation of the secondary amine functions of the N,N'-dimethyl-1,6-hexanediamine with ethylene oxide so as to lead to N,N'-dimethyl-N,N'-di(2-hydroxyethyl)-1,6-hexanediamine.

According to another embodiment, the first precursor compound is 1,6-hexanediamine and the second precursor compound is formaldehyde. The method then comprises:
- a first step of partial methylation of the 1,6-hexanediamine by reaction with formaldehyde and hydrogen, in the presence of a hydrogen catalyst, so as to form at least one intermediate compound selected from the list comprising N-methyl-1,6-hexanediamine, N,N-dimethyl-1,6-hexanediamine, N,N'-dimethyl-1,6-hexanediamine and N,N,N'-trimethyl-1,6-hexanediamine;
- a second reaction step between ethylene oxide and at least one intermediate compound so as to form at least one compound with general formula (I).

BRIEF DESCRIPTION OF THE FIGURES

Other features and advantages of the invention will be clear from reading the description hereafter of embodiments given by way of non limitative example, with reference to the accompanying figures wherein.

In the figures, the abbreviation "cat" stands for catalyst and the arrows represent reaction steps. These are reaction schemes. The illustrations of the synthesis method according to the invention do not comprise all of the components required for implementing it. Only the elements necessary for understanding the invention are shown, the person skilled in the art being able to supplement this representation for implementing the invention.

DETAILED DESCRIPTION OF THE INVENTION

The present invention relates to the synthesis of partly N-hydroxyethylated tertiary 1,6-hexanediamines with general formula (I) as follows:

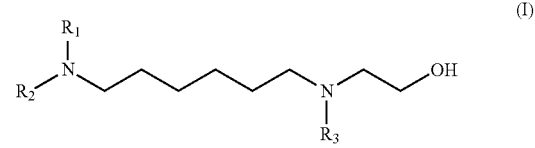

wherein:
radicals $R_1$, $R_2$, $R_3$ are each selected indiscriminately among a methyl radical and a hydroxyethyl radical, and at least one radical among $R_1$, $R_2$, $R_3$ is a methyl radical.

Preferably, radicals $R_1$ and $R_3$ are methyl radicals and radical $R_2$ is a hydroxyethyl radical, or radicals $R_2$ and $R_3$ are methyl radicals and radical $R_1$ is a hydroxyethyl radical.

At least one of the following partly N-hydroxyethylated tertiary 1,6-hexanediamines can be advantageously synthesized according to the invention:

N,N,N'-trimethyl-N'-(2-hydroxyethyl)-1,6-hexanediamine with formula ($I_1$) as follows:

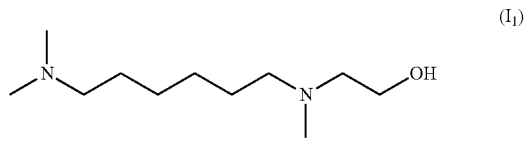

N,N'-dimethyl-N,N'-di(2-hydroxyethyl)-1,6-hexanediamine with formula ($I_2$) as follows:

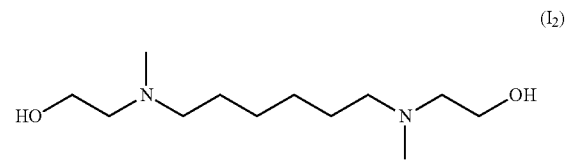 [SMILES: CN(CCO)CCCCCCN(C)CCO]

N,N-dimethyl-N',N'-di(2-hydroxyethyl)-1,6-hexanediamine with formula ($I_3$) as follows:

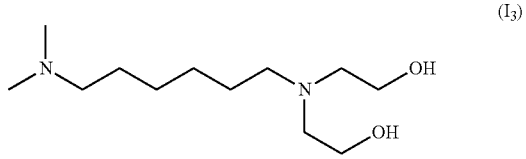 [SMILES: CN(C)CCCCCCN(CCO)CCO]

N-methyl-N,N',N'-tri(2-hydroxyethyl)-1,6-hexanediamine with formula ($I_4$) as follows:

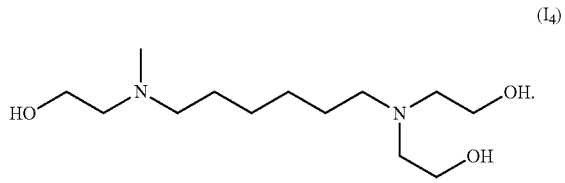 [SMILES: CN(CCO)CCCCCCN(CCO)CCO]

Synthesis from 1,6-hexanediamine

Figure 1:
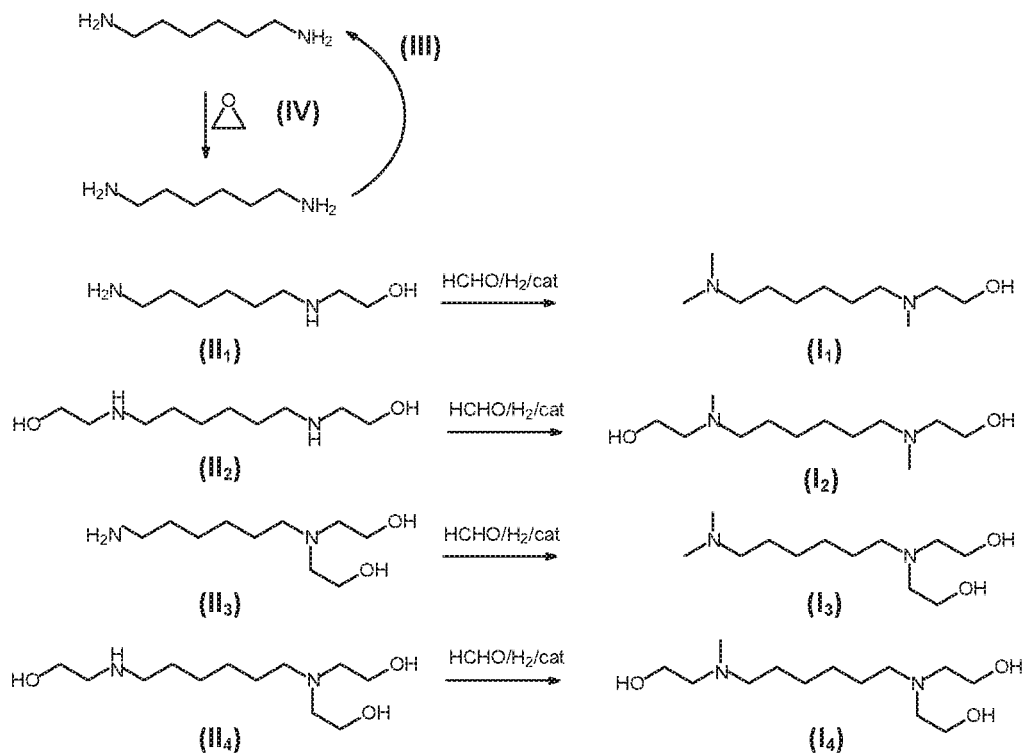
FIG. 1 shows a synthesis method for compounds of general formula (I) from 1,6-hexanediamine according to an embodiment of the invention.

FIG. 1 illustrates the synthesis of at least one compound of general formula (I) from 1,6-hexanediamine, of formula (III).

The method consists of the succession of two reaction steps from 1,6-hexanediamine.

The first step consists in reacting the 1,6-hexanediamine with ethylene oxide (formula IV) in suitable amount and conditions so as to obtain either a partly ethoxylated 1,6-hexanediamine such as N-(2-hydroxyethyl)-1,6-hexanediamine (formula $II_1$) or N-N'-di(2-hydroxyethyl)-1,6-hexanediamine (formula $II_2$) or N-N-di(2-hydroxyethyl)-1,6-hexanediamine (formula $II_3$) or N-N-N'-tri(2-hydroxyethyl)-1,6-hexanediamine (formula $II_4$), or a mixture of these molecules. These partly ethoxylated 1,6-hexanediamines of formula ($II_1$) to ($II_4$) are intermediate products in this synthesis mode.

The reaction conditions are suited in order not to obtain N,N,N',N'-tetra(2-hydroxyethyl)-1,6-hexanediamine and to minimize the amount of residual 1,6-hexanediamine. It is therefore advantageous to operate with a molar ratio of ethylene oxide to 1,6-hexanediamine not exceeding 3/1, preferably not exceeding 2.5/1. The selection of the molar ratio between the ethylene oxide and the 1,6-hexanediamine conditions the composition of the products obtained.

When residual 1,6-hexanediamine is present, it can be removed from the medium by distillation for example and optionally recycled.

When N,N,N',N'-tetra(2-hydroxyethyl)-1,6-hexanediamine is obtained, it can be removed from the medium by distillation for example.

When a mixture of intermediate compounds is obtained, it can be used as it is to carry out the second step or it can be subjected to separation, by distillation for example, in order to obtain one of the compounds of general formula (I) or a combination of these compounds (formulas $I_1$ to $I_4$) at the end of the second step.

The second step consists in the methylation of the primary or secondary amine functions of the intermediate compounds (of formulas $II_1$ to $II_4$) obtained in the first step in order to lead to N,N,N'-trimethyl-N'-(2-hydroxyethyl)-1,6-hexanediamine (formula $I_1$) and/or N,N'-dimethyl-N,N'-di(2-hydroxyethyl)-1,6-hexanediamine (formula $I_2$) and/or N,N-dimethyl-N'-N'-di(2-hydroxyethyl)-1,6-hexanediamine (formula $I_3$) and/or N-methyl-N-N'-N'-tri(2-hydroxyethyl)-1,6-hexanediamine (formula $I_4$).

Methylation of the amine functions can be achieved using any means known to the person skilled in the art, notably by reaction of formaldehyde (HCHO) and hydrogen ($H_2$) in the presence of a suitable catalyst (as shown in FIG. 1) or for example by reaction of formaldehyde and formic acid according to the reaction known as Eschweiler-Clarke reaction.

Figure 7:
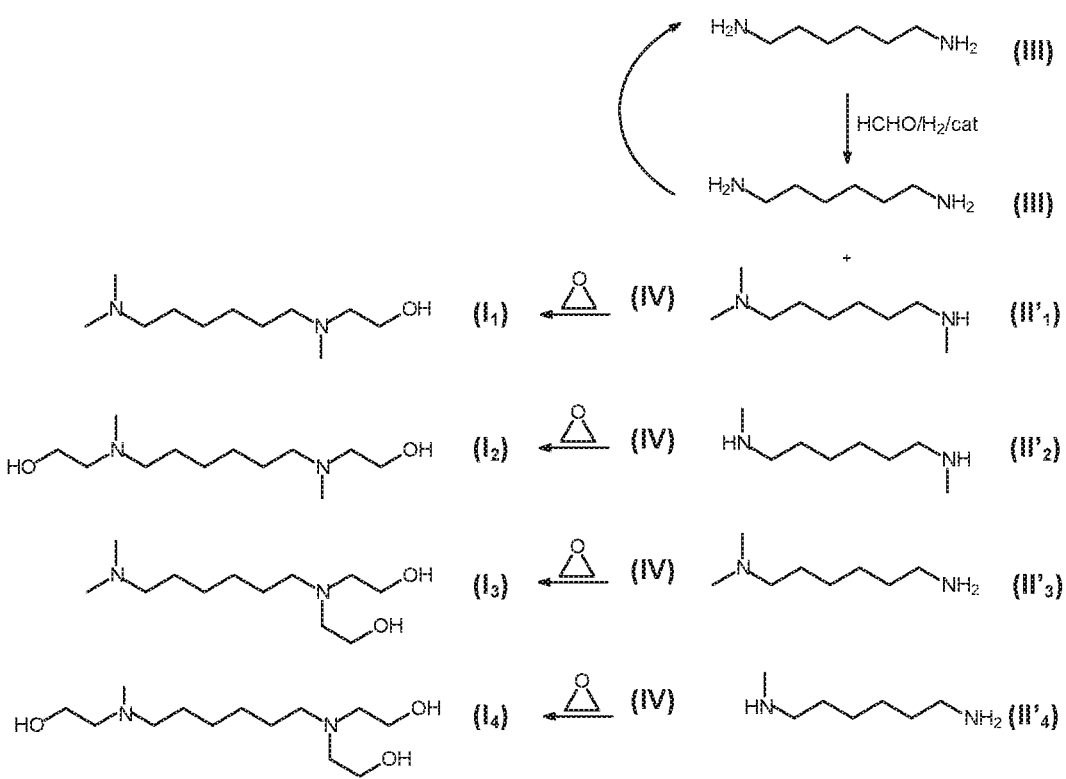
FIG. 7 shows a synthesis method for compounds of general formula (I) from 1,6-hexanediamine according to another embodiment of the invention.

According to an alternative synthesis pathway from 1,6-hexanediamine, the ethoxylation and methylation steps can be reversed in relation to the pathway described above and illustrated in FIG. 1. In this case, a first step of partial methylation of the 1,6-hexanediamine, by reaction with formaldehyde and hydrogen in the presence of a hydrogenation catalyst, leads to N-methyl-1,6-hexanediamine (formula ($II'_4$)) and/or to N,N-dimethyl-1,6-hexanediamine (formula ($II'_3$)) and/or to N,N'-dimethyl-1,6-hexanediamine (formula ($II'_2$)) and/or to N,N,N'-trimethyl-1,6-hexanediamine (formula ($II'_1$)). Then, in a second step, the primary and secondary amine functions are ethoxylated by reaction with ethylene oxide (formula (IV)). This variant of this first synthesis method is illustrated in FIG. 7.

Synthesis from 1,6-hexanediol

A compound of general formula (I) can be synthesized from 1,6-hexanediol (formula (V)).

Figure 2:
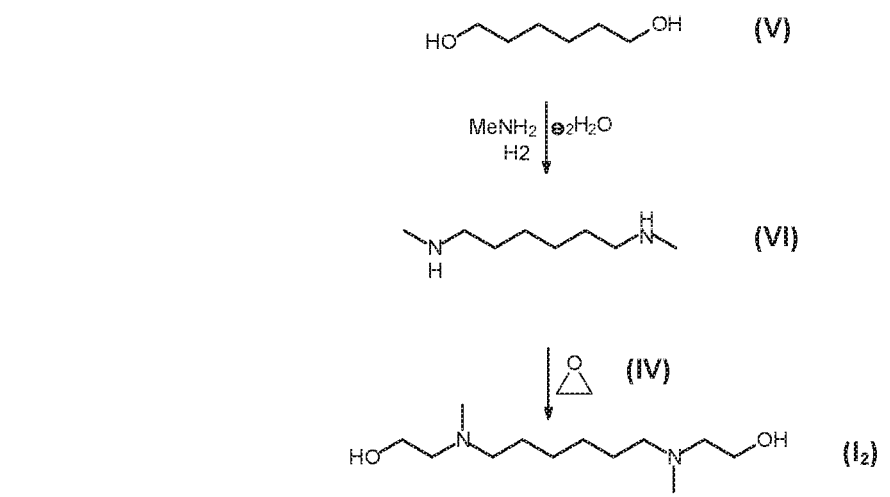
FIG. 2 shows the synthesis of N,N'-dimethyl-N,N'-di(2-hydroxyethyl)-1,6-hexane-diamine from 1,6-hexanediol according to an embodiment of the invention.

FIG. 2 illustrates the synthesis of an example of a compound with general formula (I), N,N'-dimethyl-N,N'-di(2-hydroxyethyl)-1,6-hexanediamine of formula ($I_2$), from 1,6-hexanediol of formula (V).

The synthesis consists of the succession of two reaction steps: the condensation of 1,6-hexanediol with methylamine ($MeNH_2$) generally used in excess in the presence of hydrogen and of a suitable catalyst for leading to N,N'-dimethyl-1,6-hexanediamine (formula (VI)) which is subsequently converted to N,N'-dimethyl-N,N'-di(2-hydroxyethyl)-1,6-hexanediamine (formula ($I_2$)) through an ethoxylation reaction with ethylene oxide (formula (IV)).

Synthesis from Adipaldehyde

A compound of general formula (I) can be synthesized from adipaldehyde.

Synthesis in 3 Reaction Steps

A compound of general formula (I) can be synthesized in three reaction steps from adipaldehyde (formula (VII)).

Figure 3:
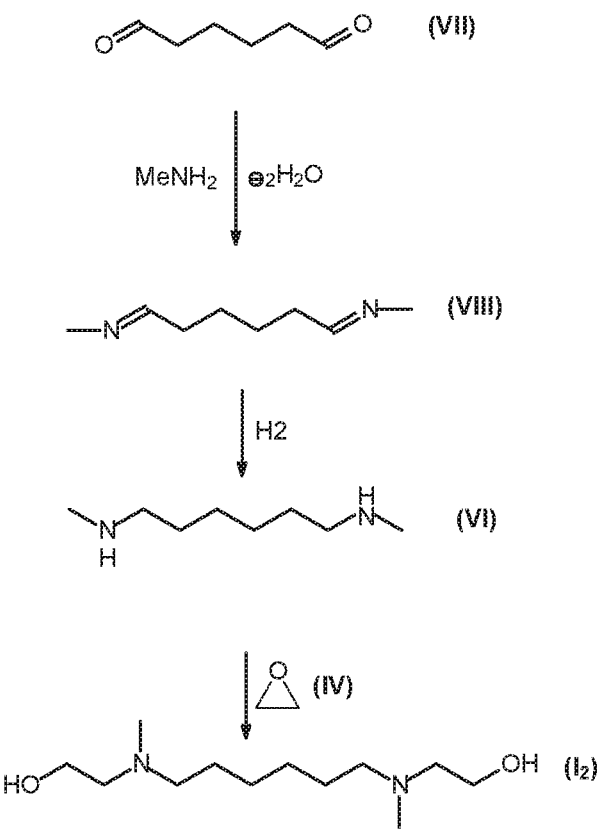
FIG. 3 shows the synthesis of N,N'-dimethyl-N,N'-di(2-hydroxyethyl)-1,6-hexane-diamine from adipaldehyde according to an embodiment of the invention (3 steps)

FIG. 3 illustrates the synthesis of an example of a compound with general formula (I), N,N'-dimethyl-N,N'-di(2-hydroxyethyl)-1,6-hexanediamine of formula ($I_2$), from adipaldehyde of formula (VII), according to a synthesis method in three reaction steps.

The synthesis consists of the succession of three reaction steps.

The first step consists in a condensation reaction of the adipaldehyde (formula (VII)) with methylamine ($MeNH_2$) leading to 1,6-bis(methylimino)-hexane (formula (VIII)).

A second reaction step consists in the reduction of the 1,6-bis(methylimino)-hexane (formula (VIII)) to N,N'-dimethyl-1,6-hexanediamine (formula (VI)).

A third reaction step consists in the ethoxylation of the N,N'-dimethyl-1,6-hexanediamine (formula (VI)) with ethylene oxide (formula (IV)) so as to form N,N'-dimethyl-N,N'-di(2-hydroxyethyl)-1,6-hexanediamine (formula ($I_2$)).

Synthesis in 1 Reaction Step

A compound of general formula (I) can be synthesized in a single reaction step from adipaldehyde (formula (VII)).

Figure 4:
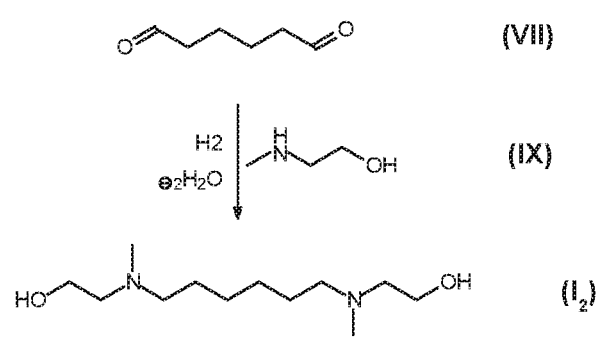
FIG. 4 shows the synthesis of N,N'-dimethyl-N,N'-di(2-hydroxyethyl)-1,6-hexane-diamine from adipaldehyde according to another embodiment of the invention (1 step)

FIG. 4 illustrates the synthesis of an example of a compound with general formula (I), N,N'-dimethyl-N,N'-di(2-hydroxyethyl)-1,6-hexanediamine of formula ($I_2$), from adipaldehyde (formula (VII)), according to a synthesis method in a single reaction step.

The synthesis consists in the condensation of the adipaldehyde (formula (VII)) with N-methyl-2-aminoethanol (formula (IX)) in the presence of hydrogen and of a suitable hydrogenation catalyst leading to N,N'-dimethyl-N,N'-di(2-hydroxyethyl)-1,6-hexane-diamine (formula ($I_2$)).

This transformation, also referred to as reductive amination, results from the succession of two reactions which are the condensation of a secondary amine with an aldehyde leading to an amine, then the hydrogenation thereof to a tertiary amine.

Synthesis from Adipic Acid or from an Adipic Acid Diester

A compound of general formula (I) can be synthesized from adipic acid or from an adipic acid diester.

Synthesis in 2 Reaction Steps

A compound of general formula (I) can be synthesized in two reaction steps from adipic acid (formula (XI)) or from an adipic acid diester such as dimethyl adipate (formula X)).

Figure 5:
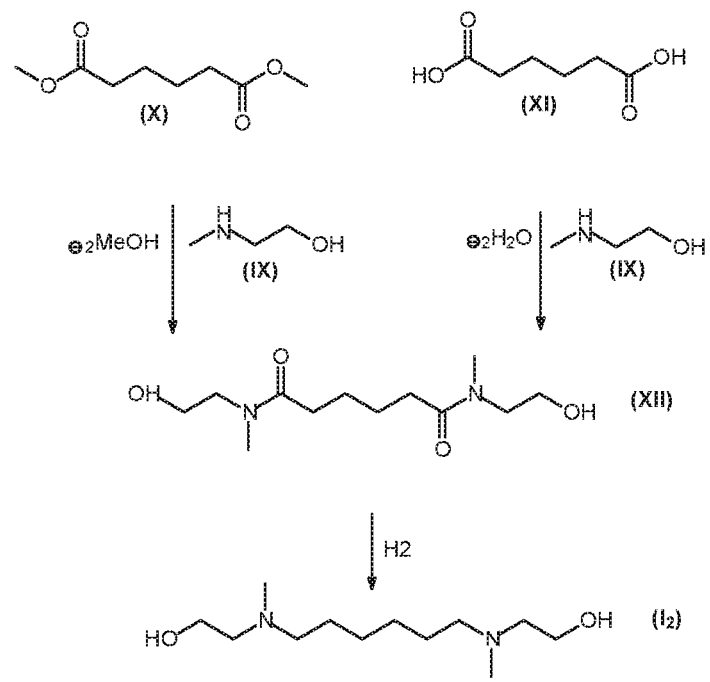
FIG. 5 shows the synthesis of N,N'-dimethyl-N,N'-di(2-hydroxyethyl)-1,6-hexane-diamine from dimethyl adipate or adipic acid according to an embodiment of the invention (2 steps)

FIG. 5 illustrates the synthesis of an example of a compound with general formula (I), N,N'-dimethyl-N,N'-di(2-hydroxyethyl)-1,6-hexanediamine of formula ($I_2$), from adipic acid (formula (XI)) or from an adipic acid diester, such as dimethyl adipate (formula (x)), according to a synthesis method in two reaction steps.

A first step consists in the condensation reaction of N-methyl-2-aminoethanol (formula (IX)) with either adipic acid (formula (XI)) or an adipic acid diester such as, by way of non limitative example, dimethyl adipate (formula (x)) or diethyl adipate. The condensation product obtained is a diamide, N,N'-dimethyl-N,N'-di(2-hydroxyethyl)-adipamide (formula (XII)).

The second step consists in the reduction of the amide functions of the N,N'-dimethyl-N,N'-di(2-hydroxyethyl)-adipamide (formula (XII)) to tertiary amine functions leading to N,N'-dimethyl-N,N'-di(2-hydroxyethyl)-1,6-hexane-diamine (formula ($I_2$)).

This reduction can be carried out by any known means such as reduction by catalytic hydrogenation or the action of hydrides such as lithium and aluminium hydride.

Synthesis in 3 Reaction Steps

A compound of general formula (I) can be synthesized in three reaction steps from adipic acid (formula (XI)) or from an adipic acid diester such as dimethyl adipate (formula X)).

Figure 6:
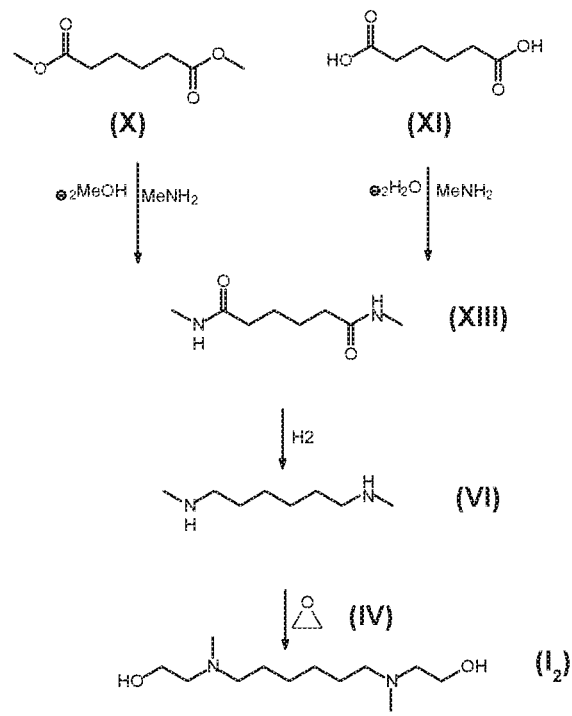
FIG. 6 shows the synthesis of N,N'-dimethyl-N,N'-di(2-hydroxyethyl)-1,6-hexane-diamine from dimethyl adipate or adipic acid according to another embodiment of the invention (3 steps)

FIG. 6 illustrates the synthesis of an example of a compound with general formula (I), N,N'-dimethyl-N,N'-di(2-hydroxyethyl)-1,6-hexanediamine of formula ($I_2$), from adipic acid (formula (XI)) or from an adipic acid diester, such as dimethyl adipate (formula (x)), according to a synthesis method in three reaction steps.

A first step consists in the condensation of methylamine ($MeNH_2$) with either adipic acid (formula (XI)) or an adipic acid diester such as, by way of non limitative example, dimethyl adipate (formula (x)) or diethyl adipate. The condensation product obtained is a diamide: N,N'-dimethyl-N,N'-adipamide of formula (XIII).

A second step consists in the reduction of the amide functions of the N,N'-dimethyl-N,N'-adipamide of formula (XIII) to tertiary amine functions leading to N,N'-dimethyl-1,6-hexanediamine (formula (VI)). This reduction can be carried out by any known means such as reduction by catalytic hydrogenation or the action of hydrides such as lithium and aluminium hydride.

A third step consists in ethoxylating the secondary amine functions of the N,N'-dimethyl-1,6-hexanediamine (formula (VI)) with ethylene oxide (formula (IV)) leading to N,N'-dimethyl-N,N'-di(2-hydroxyethyl)-1,6-hexanediamine of formula ($I_2$).

APPENDIX: LIST OF THE COMPOUND NAMES AND THEIR FORMULAS APPEARING IN THE FIGURES

APPENDIX

| Ref. | Name | Formula |
|---|---|---|
| ($I_1$) | N,N,N'-trimethyl-N'-(2-hydroxyethyl)-1,6-hexanediamine of formula ($I_1$) as follows | |
| ($I_2$) | N,N'-dimethyl-N,N'-(2-hydroxyethyl)-1,6-hexanediamine | |
| ($I_3$) | N,N-dimethyl-N',N'-di(2-hydroxyethyl)-1,6-hexanediamine | |
| ($I_4$) | N-methyl-N,N',N'-tri(2-hydroxyethyl)-1,6-hexanediamine | |
| ($II_1$) | N-(2-hydroxyethyl)-1,6-hexanediamine | |

APPENDIX-continued

List of the compound names and their formulas appearing in the figures:

| Ref. | Name | Formula |
|---|---|---|
| (II$_2$) | N-N'-di(2-hydroxyethyl)-1,6-hexanediamine | HOCH$_2$CH$_2$-NH-(CH$_2$)$_6$-NH-CH$_2$CH$_2$OH |
| (II$_3$) | N,N,-di(2-hydroxyethyl)-1,6-hexanediamine | H$_2$N-(CH$_2$)$_6$-N(CH$_2$CH$_2$OH)$_2$ |
| (II$_4$) | N-N-N'-tri(2-hydroxyethyl)-1,6-hexanediamine | HOCH$_2$CH$_2$-NH-(CH$_2$)$_6$-N(CH$_2$CH$_2$OH)$_2$ |
| (III) | 1,6-Hexanediamine | H$_2$N-(CH$_2$)$_6$-NH$_2$ |
| (IV) | Ethylene oxide | (epoxide) |
| (V) | 1,6-Hexanediol | HO-(CH$_2$)$_6$-OH |
| (VI) | N,N'-dimethyl-1,6-hexanediamine | CH$_3$NH-(CH$_2$)$_6$-NHCH$_3$ |
| (VII) | Adipaldehyde | OHC-(CH$_2$)$_4$-CHO |
| (VIII) | 1,6-bis(methylimino)-hexane | CH$_3$-N=CH-(CH$_2$)$_4$-CH=N-CH$_3$ |
| (IX) | N-methyl-2-aminoethanol | CH$_3$-NH-CH$_2$CH$_2$-OH |
| (X) | Dimethyl adipate | CH$_3$O-CO-(CH$_2$)$_4$-CO-OCH$_3$ |
| (XI) | Adipic acid | HOOC-(CH$_2$)$_4$-COOH |
| (XII) | N,N'-dimethyl-N,N'-di(2-hydroxyethyl)-adipamine | HOCH$_2$CH$_2$-N(CH$_3$)-CO-(CH$_2$)$_4$-CO-N(CH$_3$)-CH$_2$CH$_2$OH |
| (XIII) | N,N'-dimethyl-N,N'-adipamide | CH$_3$NH-CO-(CH$_2$)$_4$-CO-NHCH$_3$ |
| (II'$_1$) | N,N,N'-trimethyl-1,6-hexanediamine | (CH$_3$)$_2$N-(CH$_2$)$_6$-NHCH$_3$ |

APPENDIX-continued

List of the compound names and their formulas appearing in the figures:

| Ref. | Name | Formula |
|---|---|---|
| (II'$_2$) | N,N'-dimethyl-1,6-hexanediamine | HN⌐∼∼∼NH |
| (II'$_3$) | N,N-dimethyl-1,6-hexanediamine | ⌐N∼∼∼NH$_2$ |
| (II'$_4$) | N-methyl-1,6-hexanediamine | HN∼∼∼NH$_2$ |

The invention claimed is:

1. A synthesis method for N,N'-dimethyl-N,N'-di(2-hydroxyethyl)-1,6-hexanediamine of formula (I$_2$) as follows:

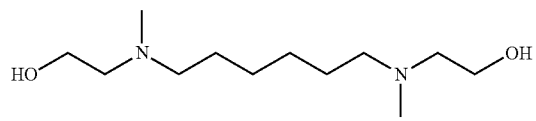 [SMILES: CN(CCO)CCCCCCN(C)CCO]

(I$_2$)

comprising two reaction steps, and
comprising at least a first reaction between a first halogen atom-free precursor compound and a second halogen atom-free precursor compound,
and wherein none of the two reaction steps comprises a halogenated organic reactant,
wherein the first halogen atom-free precursor compound being 1,6-hexanediamine and the second halogen atom-free precursor compound being ethylene oxide,
said method comprising:
a first reaction step between the 1,6-hexanediamine and the ethylene oxide so as to form at least one intermediate compound selected from the group consisting of N-(2-hydroxyethyl)-1,6-hexanediamine, N,N'-di(2-hydroxyethyl)-1,6-hexanediamine, N,N-di(2-hydroxyethyl)-1,6-hexanediamine and N,N,N'-tri(2-hydroxyethyl)-1,6-hexane-diamine;
a second step of methylation of the primary or secondary amine functions of said at least one intermediate compound so as to form at least N,N'-dimethyl-N,N'-di(2-hydroxyethyl)-1,6-hexanediamine, said second methylation step being carried out by reaction between said intermediate compound, formaldehyde and hydrogen in the presence of a hydrogenation catalyst, or by reaction between said intermediate compound, formaldehyde and formic acid according to the Eschweiler-Clarke reaction.

2. A method as claimed in claim 1, wherein any residual 1,6-hexanediamine that has not reacted at the end of the first reaction step is recycled to said first reaction step, after separation by distillation of said 1,6-hexanediamine from said at least one intermediate compound.

3. A method as claimed in claim 1, wherein the molar ratio of ethylene oxide to 1,6-hexanediamine is less than or equal to 3/1.

4. A method as claimed in claim 1, further comprising, at the end of the first reaction step, at least one separation step of at least one of said intermediate compounds or the N,N'-dimethyl-N,N'-di(2-hydroxyethyl)-1,6-hexanediamine of formula (I$_2$) at the end of the second methylation step.

5. A method as claimed in claim 2, wherein the molar ratio of ethylene oxide to 1,6-hexanediamine is less than or equal to 3/1.

6. A method as claimed in claim 2, further comprising, at the end of the first reaction step, at least one separation step of at least one of said intermediate compounds or the N,N'-dimethyl-N,N'-di(2-hydroxyethyl)-1,6-hexanediamine of formula (I$_2$) at the end of the second methylation step.

7. A method as claimed in claim 3, further comprising, at the end of the first reaction step, at least one separation step of at least one of said intermediate compounds or the N,N'-dimethyl-N,N'-di(2-hydroxyethyl)-1,6-hexanediamine of formula (I$_2$) at the end of the second methylation step.

8. A method as claimed in claim 5, further comprising, at the end of the first reaction step, at least one separation step of at least one of said intermediate compounds or the N,N'-dimethyl-N,N'-di(2-hydroxyethyl)-1,6-hexanediamine of formula (I$_2$) at the end of the second methylation step.

9. A method as claimed in claim 1, which consists of said two reaction steps.

10. A method as claimed in claim 1, wherein the molar ratio of ethylene oxide to 1,6-hexanediamine is less than or equal to 2.5/1.

11. A method as claimed in claim 1, further comprising, at the end of the first reaction step, at least one separation step by distillation of at least one of said intermediate compounds or the N,N'-dimethyl-N,N'-di(2-hydroxyethyl)-1,6-hexanediamine of formula (I$_2$) at the end of the second methylation step.

12. A method as claimed in claim 1, wherein the molar ratio of ethylene oxide to 1,6-hexanediamine is less than or equal to 2.5/1.

13. A method as claimed in claim 1, further comprising, at the end of the first reaction step, at least one separation step by distillation of at least one of said intermediate compounds or the N,N'-dimethyl-N,N'-di(2-hydroxyethyl)-1,6-hexanediamine of formula (I$_2$) at the end of the second methylation step.

14. A method as claimed in claim 2, further comprising, at the end of the first reaction step, at least one separation step by distillation of at least one of said intermediate compounds or the N,N'-dimethyl-N,N'-di(2-hydroxyethyl)-1,6-hexanediamine of formula ($I_2$) at the end of the second methylation step.

15. A method as claimed in claim 5, further comprising, at the end of the first reaction step, at least one separation step by distillation of at least one of said intermediate compounds or the N,N'-dimethyl-N,N'-di(2-hydroxyethyl)-1,6-hexanediamine of formula ($I_2$) at the end of the second methylation step.

\* \* \* \* \*